US00PP16615P2

(12) United States Plant Patent
Griffith

(10) Patent No.: US PP16,615 P2
(45) Date of Patent: Jun. 6, 2006

(54) *LOROPETALUM* PLANT NAMED 'GRIFFCRL'

(50) Latin Name: ***Loropetalum chinense* var. *rubrum***
Varietal Denomination: GriffCRL

(75) Inventor: Mark P. Griffith, Watkinsville, GA (US)

(73) Assignee: Griffith Propagation Nursery, Watkinsville, GA (US)

( * ) Notice: Subject to any disclaimer, the term of this patent is extended or adjusted under 35 U.S.C. 154(b) by 109 days.

(21) Appl. No.: 11/068,078

(22) Filed: Feb. 28, 2005

(51) Int. Cl.
*A01H 5/00* (2006.01)

(52) U.S. Cl. ..... Plt./226

(58) Field of Classification Search ..... Plt./226
See application file for complete search history.

*Primary Examiner*—Anne Marie Grunberg
(74) *Attorney, Agent, or Firm*—Jondle & Associates P.C.

(57) ABSTRACT

A *Loropetalum chinense* var. *rubrum* cultivar particularly distinguished by having a compact growth habit, vibrant fuchsia flower color, abundant flowers and tolerance to heavy rain, high wind and ice is disclosed.

2 Drawing Sheets

Genus and species: *Loropetalum chinense* var. *rubrum*.
Variety denomination: 'GriffCRL'.

BACKGROUND OF THE NEW PLANT

The present invention comprises a new and distinct cultivar of *Loropetalum,* botanically known as *Loropetalum chinense* var. *rubrum,* and hereinafter referred to by the cultivar name 'GriffCRL'. The new cultivar was discovered as a naturally-occurring branch mutation of the *Loropetalum chinense* var. *rubrum* cultivar 'Ruby' (unpatented) in Watkinsville, Ga. in 1996.

The genus *Loropetalum* is included in the family Hamamelidaceae that comprises about 15 genera of shrubs and trees growing in the northern hemisphere. *Loropetalum* comprises one species of evergreen shrub or small tree which possesses desirable ornamental characteristics. *Loropetalum* was first introduced to Europe as an ornamental plant in the 1880s and is believed to have been cultivated in North America since the early 1930s. *Loropetalum chinense* var. *rubrum* is a native of China and was first discovered in 1928 in Hunan Province. It was rediscovered in the late 1980s and subsequently introduced to the United States.

Asexual reproduction of the new cultivar by stem cuttings at Watkinsville, Ga. since June, 1996, has shown that the distinctive features of this new *Loropetalum* are stable and reproduce true to type in successive generations of asexual propagation.

DESCRIPTION OF THE PHOTOGRAPHS

This new *Loropetalum* plant is illustrated by the accompanying photographs which show the plant's form, foliage and flowers. The colors shown are as true as can be reasonably obtained by conventional photographic procedures.

Figure 1:
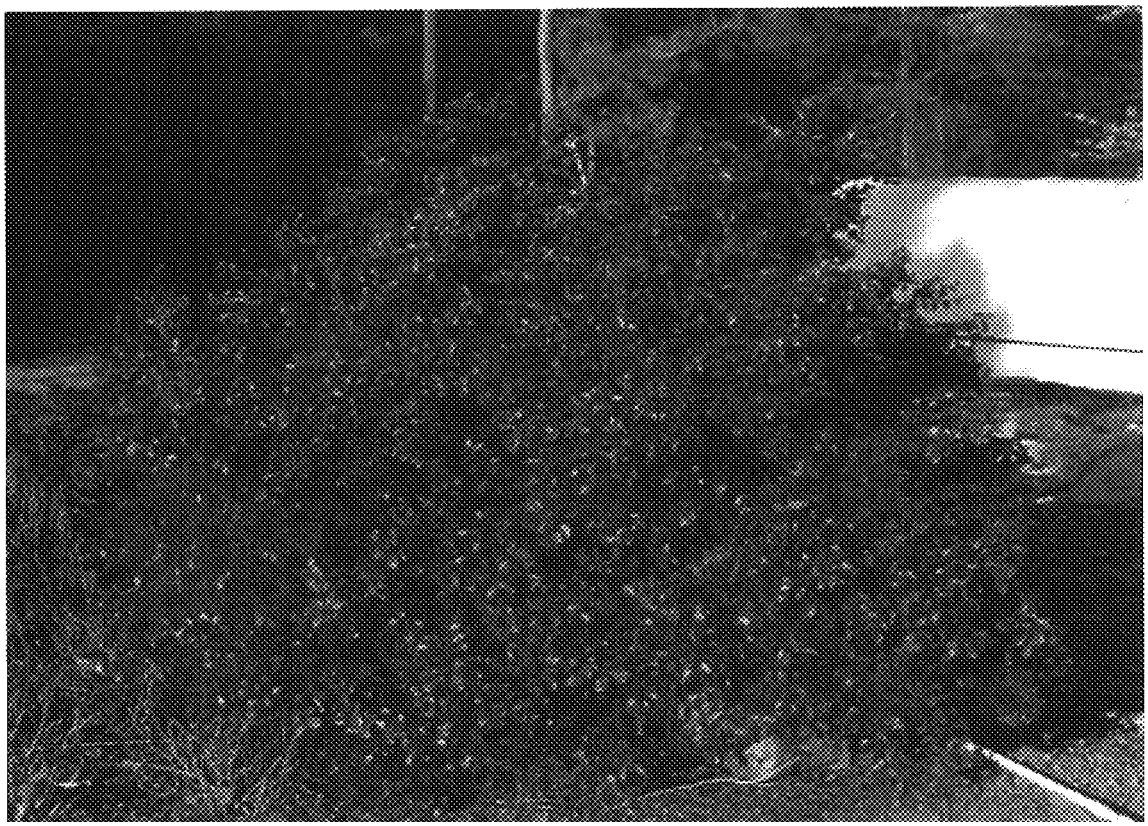

FIG. 1. shows the mature plant's form, foliage and flowers.

Figure 2:
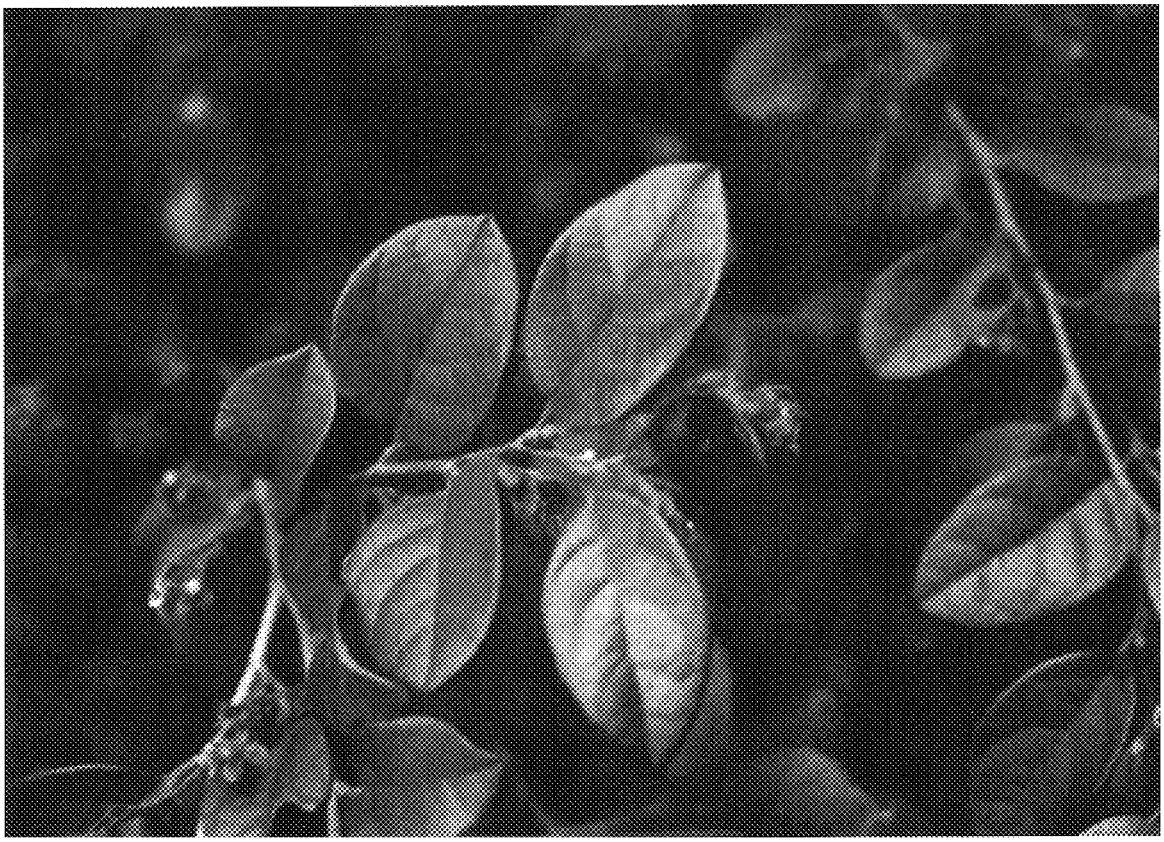

FIG. 2. shows a closer view of the flowers.

DESCRIPTION OF THE NEW CULTIVAR

The following detailed description sets forth the distinctive characteristics of 'GriffCRL'. The data which define these characteristics were collected from asexual reproductions carried out in Watkinsville, Ga. The detailed description was taken on 7-year-old plants grown in the ground. Color readings were taken in natural light. Color references are to the Colour Chart of The Royal Horticultural Society of London (R.H.S.), 2001 edition.

DETAILED BOTANICAL DESCRIPTION

Classification:
- *Family.*—Hamamelidaceae.
- *Botanical name.*—*Loropetalum chinense* var. *rubrum* 'GriffCRL'.
- *Common name.*—Chinese fringe flower; Asian witch hazel.

Parentage: Naturally-occurring branch mutation of *Loropetalum chinense* var. *rubrum* 'Ruby' (unpatented).

Plant description:
- *Type.*—Perennial, evergreen shrub.
- *Form.*—Rounded.
- *Habit.*—Multi-trunked with horizontal branches forming a rounded shape.
- *Height.*—5–6 feet.
- *Width.*—11–12 feet.

Propagation:
- *Type.*—Vegetative cuttings.
- *Time to initiate roots, summer.*—28 days at 29° C.
- *Time to initiate roots, winter.*—35 days at 21° C.
- *Time to produce a rooted young plant, summer.*—56 days at 29° C.
- *Time to produce a rooted young plant, winter.*—72 days at 21° C.
- *Root description.*—Thick, fibrous, freely branching; fleshy new roots.

Growing conditions: Does well in full sun and tolerates temperatures from −13° C. to 38° C. Requires yearly fertilization with a slow-release fertilizer. This plant tolerates heavy rain, high wind and ice due to its strong, compact branching habit.

Branches:

*Habit.*—Planar branches at 180° from trunks.
*Number.*—31.
*Length.*—6 feet.
*Diameter.*—0.1 cm at 2.5 cm from branch tip; 0.3 cm at 30.5 cm from tip.
*Internode length.*—1.5 cm.
*Shape.*—Round.
*Color.*—New growth: RHS 183A (gray-purple). First-year growth: RHS 199A (gray-brown). Second-year growth: RHS 200C (brown).
*Pubescence.*—New growth: Evenly pubescent. First and second year: Pubescent in fissures. Lenticels: Present on second-year and older wood.

Leaves:

*Arrangement.*—Alternate.
*Type.*—Single.
*Number per lateral branch.*—700.
*Shape.*—Elliptical.
*Margin.*—Entire.
*Apex.*—Acute.
*Base.*—Oblique.
*Length.*—3.31 cm.
*Width.*—2.12 cm.
*Texture.*—Upper surface: Rough, sandpaper-like. Lower surface: Rough, but not as rough as upper surface.
*Pubescence.*—Upper surface: Present on veins, sparse between veins. Lower surface: Sparse.
*Venation.*—Pinnate.
*Color.*—Immature leaves: Upper surface: RHS 183C (gray-purple). Lower surface: RHS 183D (gray-purple). Mature leaves: Upper surface: RHS 186A (gray-purple) with RHS 199A (gray-brown) midvein and RHS 199D (gray-brown) lateral veins. Lower surface: RHS 187B (gray-purple) with RHS 62C (red-purple) midvein and RHS 62D (red-purple) lateral veins.

Petioles:

*Length.*—0.3 cm.
*Diameter.*—0.1 cm.
*Texture.*—Pubescent.
*Color.*—RHS 199A (gray-brown).
*Stipules.*—At first and second nodes from end of new growth; not always present. Stipule length: 0.4 cm. Stipule width: 0.1 cm. Stipule color: RHS 183A (gray-purple).

Inflorescence:

*Type.*—Cyme.
*Length.*—2 cm.
*Width.*—4 cm.
*Habit.*—Configuration of florets forms an upright, rounded umbel; the strap-shaped petals of the florets result in a pom-pom-like appearance.
*Number of florets per inflorescence.*—8.
*Number of inflorescences per lateral branch.*—2,000.
*Inflorescence coverage per plant.*—90% of plant is covered in flowers during flowering period.
*Flowering period.*—March–April for 2 weeks; flowers again in October.
*Lastingness of flowers.*—4–5 days.
*Fragrance.*—None.

Inflorescence buds:

*Number of buds per lateral branch.*—2,000.
*Bud length.*—0.15 cm.
*Bud width.*—0.15 cm.
*Bud shape.*—Orbicular.
*Bud color.*—RHS 77D (purple).

Petals:

*Arrangement.*—Opposite.
*Number.*—4–6.
*Shape.*—Strap-shaped.
*Margin.*—Entire.
*Apex.*—Blunt, sometimes notched.
*Length.*—2 cm.
*Width.*—0.1 cm.
*Texture.*—Silky, both surfaces.
*Color.*—When opening: RHS 60A (red-purple), both surfaces. When fully opened: RHS 61B (red-purple), both surfaces. Fading to: RHS 83A (violet).

Sepals:

*Arrangement.*—Cruciform.
*Number.*—4.
*Shape.*—Triangular.
*Margin.*—Entire.
*Apex.*—Acute, curling outward.
*Base.*—Fused onto calyx cup.
*Length.*—0.2 cm.
*Width.*—0.2 cm.
*Texture.*—Pubescent.
*Color.*—Immature: Upper surface: RHS 64D (red-purple). Lower surface: RHS 59D (red-purple). Mature: RHS 177A (gray-orange), both surfaces.

Calyx and peduncle:

*Calyx.*—Shape: Urn. Length: 0.2 cm. Width: 0.15 cm.
*Peduncle.*—Length: 0.5 cm. Width: 0.1 cm. Angle: 45 degrees from stem.

Reproductive organs:

*Stamens.*—Number: 4. Anther shape: Round. Anther length: 0.05 cm. Anther width: 0.05 cm. Anther color: RHS 79B (purple). Pollen: Minimal. Pollen color: RHS 155A (white).
*Pistils.*—Number: 1–2. Length: 0.1 cm. Stigma shape: Oval to urn. Stigma color: RHS 59D (red-purple). Style length: 0.075 cm. Style color: RHS 59D (red-purple). Ovary color: RHS 59D (red-purple).

Seeds:

*Number.*—1–2.
*Length.*—0.6 cm.
*Width.*—0.3 cm.
*Color.*—RHS 202A (black).

Fruit:

*Type.*—Two-horned capsule.
*Number.*—3–5 per lateral branch.
*Number per plant.*—100.
*Length.*—1.2 cm.
*Width.*—0.6 cm.
*Color.*—RHS 177B (gray-orange).
*Texture.*—Woody.
*Length of ripening.*—4 months.

Disease and insect resistance: No known pests. No leaf spot or other foliage diseases observed. Not susceptible to root rot under normal conditions.

COMPARISON WITH MUTATION PARENT

*Loropetalum chinense* var. *rubrum* 'GriffCRL' is a distinct variety of *Loropetalum* due to its compact habit, vibrant fuchsia flower color and abundant flowers. The closest comparison plant to 'GriffCRL' is its mutation parent 'Ruby', however it is distinguished from 'Ruby' by its smaller size, brighter flower color and the following characteristics listed in Table 1 below.

TABLE 1

| Characteristic | 'GriffCRL' | 'Ruby' |
|---|---|---|
| Growth Habit | Multi-trunked; branches at 180° angle | Multi-trunked; branches at 45° angle |
| Plant Height | 5–6 feet | 12 feet |
| Plant Diameter | 11–12 feet | 10 feet |
| Growth rate | Slow | Fast |
| Number lateral branches | 31 | 53 |
| Lateral branch length | 6 feet | 4.5 feet |
| Leaf length | 3.31 cm | 2.92 cm |
| Leaf width | 2.12 cm | 2.06 cm |

TABLE 1-continued

| Characteristic | 'GriffCRL' | 'Ruby' |
|---|---|---|
| Leaf color, mature leaf, upper surface | RHS 186A (gray-purple) | RHS 147A (yellow-green) |
| Leaf color, mature leaf, lower surface | RHS 187B (gray-purple) | RHS 147B (yellow-green) |
| Inflorescence coverage per plant, spring | 90% | 80% |
| Inflorescence coverage per plant, fall | 20% | 10% |

I claim:

1. A new and distinct *Loropetalum* plant as shown and described herein.

* * * * *